(12) United States Patent
Zhang et al.

(10) Patent No.: US 7,718,626 B2
(45) Date of Patent: May 18, 2010

(54) ERBB3 BINDING PROTEIN COMPOSITIONS AND METHODS OF USE

(75) Inventors: Yue-xing Zhang, Ellicott City, MD (US); Anne W. Hamburger, Baltimore, MD (US)

(73) Assignee: University of Maryland, Baltimore, Baltimore, MD (US)

(*) Notice: Subject to any disclaimer, the term of this patent is extended or adjusted under 35 U.S.C. 154(b) by 389 days.

(21) Appl. No.: 11/357,295

(22) Filed: Feb. 17, 2006

(65) Prior Publication Data

US 2006/0182719 A1 Aug. 17, 2006

Related U.S. Application Data

(60) Provisional application No. 60/653,733, filed on Feb. 17, 2005.

(51) Int. Cl.
  *A61K 48/00* (2006.01)
  *C12N 15/86* (2006.01)

(52) U.S. Cl. ........................ 514/44; 424/93.2

(58) Field of Classification Search ....................... None
See application file for complete search history.

(56) References Cited

U.S. PATENT DOCUMENTS

2002/0044941 A1* 4/2002 Rosen et al. ............. 424/184.1

OTHER PUBLICATIONS

Horvath et al (EMBO Journal, 2006, 25:4909-4920).*
Nabel (PNAS, 1999, 96:324-326).*
Lessor et al (J of Cellular Physiology, 2000, 183:321-329).*
Zhang et al (Nucleic Acids Research, 2003, 8:2168-2177).*
Zhang et al I (2003, Nucleic Acids Research, 2003, 31:2168-2177).*
Zhang et al II (Nucleic Acids Research, 2005, 33:6024-6033).*
Liu et al (PNAS, 2006, 103:10917-10922).*
Saskia et al (J of Immunology, 2007, 179:2005-2012).*
Rolland (Advanced Drug Delivery Reviews, 2005, 57:669-673).*
McNeish et al (Gene Therapy, 2004, 11:497-503).*
McCormick (Nature Reviews, 2001, 1:130-141).*
Jones et al, J of Biological Chemistry, 1998, 273:11667-11674.*
Kinogasa et al, Biochemical and Biophysical Research Communications, 2004, 321:1045-1049.*
Squatrito et al (Oncogene, 2004, 23:4454-4465).*
Xia et al (J of Cellular Physiology, 2001, 187:209-217).*
Lessor et al (J Cellular Physiology, 2000, 183:321-329).*
Zhang et al (J Biological Chemistry, 2004, 279:26126-26133).*
Christiansen et al (Mol Cancer Ther, 2004, 3:1493-1501).*
Topp et al (Journal of Controlled Release, 1998, 53:15-23).*
Zhang et al (PNAS, 2005, 102:9890-9895, IDS).*
Scardino (New England Journal of Medicine, 2003, 349: 297-299).*
American Heritage® Dictionary of the English Language (fourth edition, 2000, web pp. 1-2).*
Zhang et al (Oncogene, 2002, 21:5609-5618, IDS).*
Xia, et al. "Analysis of the Expression Pattern of Ebp1, an ErbB-3-Binding Protein" *Biochemical and Biophysical Research Communications*, vol. 289, pp. 240-244 (2001).
Yoo et al. "Interaction of the PA2G4 (EBP1) protein with ErbB-3 and regulation of this binding by heregulin" *British Journal of Cancer*, vol. 82 (3), pp. 683-690 (2000).
Zhang et al. "The ErbB3-binding protein Ebp1 suppresses androgen receptor-mediated gene transcription and tumorigenesis of prostate cancer cells" *PNAS*, vol. 102 (28), pp. 9890-9895 (Jul. 12, 2005).
Zhang et al. "Repression of androgen receptor mediated transcription by the ErbB-3 binding protein, Ebp1" *Oncogene*, vol. 21, pp. 5609-5618 (2002).
NCBI, *GenBank*, Accession No. NM-006191.

* cited by examiner

*Primary Examiner*—Laura B Goddard
(74) *Attorney, Agent, or Firm*—Whitham, Curtis, Christofferson & Cook, P.C.

(57) ABSTRACT

A method of repressing a cell-cycle gene, which is regulated by an E2F transcription factor, in a cell, wherein the method comprises contacting the cell with a cell-cycle gene-repressing amount of ErbB3 binding protein (Ebp1); a method of inhibiting prostate cancer in a mammal, wherein the method comprises administering to the mammal a prostate cancer-inhibiting amount of Ebp1; a composition comprising an Ebp1-expressing viral vector that expresses a cell-cycle gene-repressing amount of Ebp1; and a composition comprising polymer-packaged DNA comprising and expressing a cell-cycle gene-repressing amount of Ebp1.

24 Claims, 2 Drawing Sheets

FIG. 1

| | |
|---|---|
| 1 | ggatcgaggg gactctgacc acagcctgtg gctgggaagg gagacagagg cggcggcggc |
| 61 | tcaggggaaa cgaggctgca gtggtggtag taggaagatg tcgggcgagg acgagcaaca |
| 121 | ggagcaaact atcgctgagg acctggtcgt gaccaagtat aagatggggg gcgacatcgc |
| 181 | caacagggta cttcggtcct tggtggaagc atctagctca ggtgtgtcgg tactcagcct |
| 241 | gtgtgagaaa ggtgatgcca tgattatgga agaaacaggg aaaatcttca agaaagaaaa |
| 301 | ggaaatgaag aaaggtattg cttttcccac cagcatttcg gtaataact gtgtatgtca |
| 361 | cttctcccct tgaagagcg accaggatta tattctcaag gaaggtgact tggtaaaaat |
| 421 | tgaccttggg gtccatgtgg atggcttcat cgctaatgta gctcacactt tgtggttga |
| 481 | tgtagctcag gggacccaag taacagggag gaaagcagat gttattaagg cagctcacct |
| 541 | ttgtgctgaa gctgccctac gcctggtcaa acctggaaat cagaacacac aagtgacaga |
| 601 | agcctggaac aaagttgccc actcatttaa ctgcacgcca atagaaggta tgctgtcaca |
| 661 | ccagttgaag cagcatgtca tcgatggaga aaaaaccatt atccagaatc ccacagacca |
| 721 | gcagaagaag gaccatgaaa aagctgaatt tgaggtacat gaagtatatg ctgtggatgt |
| 781 | tctcgtcagc tcaggagagg gcaaggccaa ggatgcagga cagagaacca ctatttacaa |
| 841 | acgagacccc tctaaacagt atggactgaa aatgaaaact tcacgtgcct tcttcagtga |
| 901 | ggtggaaagg cgttttgatg ccatgccgtt tactttaaga gcatttgaag atgagaagaa |
| 961 | ggctcggatg ggtgtggtgg agtgcgccaa acatgaactg ctgcaaccat ttaatgttct |
| 1021 | ctatgagaag gagggtgaat ttgttgccca gtttaaattt acagttctgc tcatgcccaa |
| 1081 | tggccccatg cggataacca gtggtcccct cgagcctgac ctctacaagt ctgagatgga |
| 1141 | ggtccaggat gcagagctaa aggccctcct ccagagttct gcaagtcgaa aaacccagaa |
| 1201 | aaagaaaaaa aagaaggcct ccaagactgc agagaatccc accagtgggg aaacattaga |
| 1261 | agaaaatgaa gctggggact gaggtgcgtc ccatctcccc agcttgctgc tcctgcctca |
| 1321 | tccccttccc accaaacccc agactctgtg aagtgcagtt cttctccacc taggaccgcc |
| 1381 | agcagagcgg ggggatctcc ctgccccac cccagttccc caacccactc ccttccaaca |
| 1441 | acaaccagct ccaactgact ctggtcttgg gaggtgaggc ttcccaacca cggaagacta |
| 1501 | ctttaaacga aaaaagaaa ttgaataata aaatcaggag tcaaaattca tcgtcttcaa |
| 1561 | ggccctctt tctagccttt tctactactc tctgcttggt caaggtttgt gccccactac |
| 1621 | agaacagggc taaattagcc accaccactg aaaactcagc cgaattttt tataccactc |
| 1681 | tgacgtcagc attttt (SEQ ID NO: 1) |

FIG. 2

MSGEDEQQEQTIAEDLVVTKYKMGGDIANRVLRSLVEASSSGVS
VLSLCEKGDAMIMEETGKIFKKEKEMKKGIAFPTSISVNNCVCHFSPLKSDQDYILKE
GDLVKIDLGVHVDGFIANVAHTFVVDVAQGTQVTGRKADVIKAAHLCAEAALRLVKPG
NQNTQVTEAWNKVAHSFNCTPIEGMLSHQLKQHVIDGEKTIIQNPTDQQKKDHEKAEF
EVHEVYAVDVLVSSGEGKAKDAGQRTTIYKRDPSKQYGLKMKTSRAFFSEVERRFDAM
PFTLRAFEDEKKARMGVVECAKHELLQPFNVLYEKEGEFVAQFKFTVLLMPNGPMRIT
SGPFEPDLYKSEMEVQDAELKALLQSSASRKTQKKKKKKASKTAENPTSGETLEENEA
GD (SEQ ID NO: 2)

SEQUENCE LISTING

<160> NUMBER OF SEQ ID NOS: 15

<210> SEQ ID NO 1
<211> LENGTH: 1697
<212> TYPE: DNA
<213> ORGANISM: Homo Sapien

<400> SEQUENCE: 1

```
ggatcgaggg gactctgacc acagcctgtg gctgggaagg gagacagagg cggcggcggc      60 tcagggaaa  cgaggctgca gtggtggtag taggaagatg tcgggcgagg acgagcaaca     120
ggagcaaact atcgctgagg acctggtcgt gaccaagtat aagatggggg gcgacatcgc     180
caacagggta cttcggtcct tggtggaagc atctagctca ggtgtgtcgg tactcagcct     240
gtgtgagaaa ggtgatgcca tgattatgga agaaacaggg aaaatcttca agaaagaaaa     300
ggaaatgaag aaaggtattg cttttcccac cagcatttcg gtaaataact gtgtatgtca     360
cttctcccct ttgaagagcg accaggatta tattctcaag gaaggtgact tggtaaaaat     420
tgaccttggg gtccatgtgg atggcttcat cgctaatgta gctcacactt ttgtggttga     480
tgtagctcag gggacccaag taacagggag gaaagcagat gttattaagg cagctcacct     540
ttgtgctgaa gctgccctac gcctggtcaa acctggaaat cagaacacac aagtgacaga     600
agcctggaac aaagttgccc actcatttaa ctgcacgcca atagaaggta tgctgtcaca     660
```

-continued

```
ccagttgaag cagcatgtca tcgatggaga aaaaaccatt atccagaatc ccacagacca      720
gcagaagaag gaccatgaaa aagctgaatt tgaggtacat gaagtatatg ctgtggatgt      780
tctcgtcagc tcaggagagg gcaaggccaa ggatgcagga cagagaacca ctatttacaa      840
acgagacccc tctaaacagt atggactgaa atgaaaact  tcacgtgcct tcttcagtga      900
ggtggaaagg cgttttgatg ccatgccgtt tactttaaga gcatttgaag atgagaagaa      960
ggctcggatg ggtgtggtgg agtgcgccaa acatgaactg ctgcaaccat ttaatgttct     1020
ctatgagaag gagggtgaat tgttgccca  gtttaaattt acagttctgc tcatgcccaa     1080
tggccccatg cggataacca gtggtccctt cgagcctgac ctctacaagt ctgagatgga     1140
ggtccaggat gcagagctaa aggccctcct ccagagttct gcaagtcgaa aacccagaa      1200 aaagaaaaaa aagaaggcct ccaagactgc agagaatccc accagtgggg aaacattaga     1260
agaaaatgaa gctggggact gaggtgcgtc ccatctcccc agcttgctgc tcctgcctca     1320 tcccttccc  accaaacccc agactctgtg aagtgcagtt cttctccacc taggaccgcc     1380
agcagagcgg ggggatctcc ctgcccccac cccagttccc caacccactc ccttccaaca     1440
acaaccagct ccaactgact ctggtcttgg gaggtgaggc ttcccaacca cggaagacta     1500
ctttaaacga aaaaagaaa  ttgaataata aaatcaggag tcaaaattca tcgtcttcaa     1560
ggcccctctt tctagccttt tctactactc tctgcttggt caaggtttgt gccccactac     1620
agaacagggc taaattagcc accaccactg aaaactcagc cgaattttt  tataccactc     1680 tgacgtcagc atttttt                                                    1697
```

<210> SEQ ID NO 2
<211> LENGTH: 394
<212> TYPE: PRT
<213> ORGANISM: Homo Sapien

<400> SEQUENCE: 2

```
Met Ser Gly Glu Asp Glu Gln Gln Glu Gln Thr Ile Ala Glu Asp Leu
1               5                   10                  15

Val Val Thr Lys Tyr Lys Met Gly Gly Asp Ile Ala Asn Arg Val Leu
            20                  25                  30

Arg Ser Leu Val Glu Ala Ser Ser Gly Val Ser Val Leu Ser Leu
        35                  40                  45

Cys Glu Lys Gly Asp Ala Met Ile Met Glu Glu Thr Gly Lys Ile Phe
    50                  55                  60

Lys Lys Glu Lys Glu Met Lys Lys Gly Ile Ala Phe Pro Thr Ser Ile
65                  70                  75                  80

Ser Val Asn Asn Cys Val Cys His Phe Ser Pro Leu Lys Ser Asp Gln
                85                  90                  95

Asp Tyr Ile Leu Lys Glu Gly Asp Leu Val Lys Ile Asp Leu Gly Val
            100                 105                 110

His Val Asp Gly Phe Ile Ala Asn Val Ala His Thr Phe Val Val Asp
        115                 120                 125

Val Ala Gln Gly Thr Gln Val Thr Gly Arg Lys Ala Asp Val Ile Lys
    130                 135                 140

Ala Ala His Leu Cys Ala Glu Ala Ala Leu Arg Leu Val Lys Pro Gly
145                 150                 155                 160

Asn Gln Asn Thr Gln Val Thr Glu Ala Trp Asn Lys Val Ala His Ser
                165                 170                 175

Phe Asn Cys Thr Pro Ile Glu Gly Met Leu Ser His Gln Leu Lys Gln
            180                 185                 190
```

```
His Val Ile Asp Gly Glu Lys Thr Ile Ile Gln Asn Pro Thr Asp Gln
        195                 200                 205

Gln Lys Lys Asp His Glu Lys Ala Glu Phe Glu Val His Glu Val Tyr
        210                 215                 220

Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
                245                 250                 255

Leu Lys Met Lys Thr Ser Arg Ala Phe Phe Ser Glu Val Glu Arg Arg
            260                 265                 270

Phe Asp Ala Met Pro Phe Thr Leu Arg Ala Phe Glu Asp Glu Lys Lys
            275                 280                 285

Ala Arg Met Gly Val Val Glu Cys Ala Lys His Glu Leu Leu Gln Pro
        290                 295                 300

Phe Asn Val Leu Tyr Glu Lys Glu Gly Glu Phe Val Ala Gln Phe Lys
305                 310                 315                 320

Phe Thr Val Leu Leu Met Pro Asn Gly Pro Met Arg Ile Thr Ser Gly
                325                 330                 335

Pro Phe Glu Pro Asp Leu Tyr Lys Ser Glu Met Glu Val Gln Asp Ala
            340                 345                 350

Glu Leu Lys Ala Leu Leu Gln Ser Ser Ala Ser Arg Lys Thr Gln Lys
            355                 360                 365

Lys Lys Lys Lys Lys Ala Ser Lys Thr Ala Glu Asn Pro Thr Ser Gly
        370                 375                 380

Glu Thr Leu Glu Glu Asn Glu Ala Gly Asp
385                 390

<210> SEQ ID NO 3
<211> LENGTH: 39
<212> TYPE: DNA
<213> ORGANISM: Artificial
<220> FEATURE:
<223> OTHER INFORMATION: Synthetic

<400> SEQUENCE: 3
ggccagtgaa ttgtaatacg actcactata gggaggcgg                            39

<210> SEQ ID NO 4
<211> LENGTH: 16
<212> TYPE: DNA
<213> ORGANISM: Artificial
<220> FEATURE:
<223> OTHER INFORMATION: Synthetic

<400> SEQUENCE: 4
gcacgccaat agaagg                                                     16

<210> SEQ ID NO 5
<211> LENGTH: 17
<212> TYPE: DNA
<213> ORGANISM: Artificial
<220> FEATURE:
<223> OTHER INFORMATION: Synthetic

<400> SEQUENCE: 5
gtaaacggca tggcatc                                                    17

<210> SEQ ID NO 6
<211> LENGTH: 21
```

-continued

```
<212> TYPE: DNA
<213> ORGANISM: Artificial
<220> FEATURE:
<223> OTHER INFORMATION: Synthetic

<400> SEQUENCE: 6
aaggctatga atgtcagccc a                                              21

<210> SEQ ID NO 7
<211> LENGTH: 22
<212> TYPE: DNA
<213> ORGANISM: Artificial
<220> FEATURE:
<223> OTHER INFORMATION: Synthetic

<400> SEQUENCE: 7
cattgaggct agagagcaag gc                                             22

<210> SEQ ID NO 8
<211> LENGTH: 17
<212> TYPE: DNA
<213> ORGANISM: Artificial
<220> FEATURE:
<223> OTHER INFORMATION: Synthetic

<400> SEQUENCE: 8
catccagtct cggattg                                                   17

<210> SEQ ID NO 9
<211> LENGTH: 19
<212> TYPE: DNA
<213> ORGANISM: Artificial
<220> FEATURE:
<223> OTHER INFORMATION: Synthetic

<400> SEQUENCE: 9
ctcatattgt agagcgggt                                                 19

<210> SEQ ID NO 10
<211> LENGTH: 18
<212> TYPE: DNA
<213> ORGANISM: Artificial
<220> FEATURE:
<223> OTHER INFORMATION: Synthetic

<400> SEQUENCE: 10
agtgctgtgt tcgccttg                                                  18

<210> SEQ ID NO 11
<211> LENGTH: 18
<212> TYPE: DNA
<213> ORGANISM: Artificial
<220> FEATURE:
<223> OTHER INFORMATION: Synthetic

<400> SEQUENCE: 11
cacctcagag ccgctaag                                                  18

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12
```

```
-continued gctatccagg ctgtgctatc                                               20

<210> SEQ ID NO 13
<211> LENGTH: 17
<212> TYPE: DNA
<213> ORGANISM: Artificial
<220> FEATURE:
<223> OTHER INFORMATION: Synthetic

<400> SEQUENCE: 13
tgtcacgcac gatttcc                                                  17

<210> SEQ ID NO 14
<211> LENGTH: 20
<212> TYPE: DNA
<213> ORGANISM: Artificial
<220> FEATURE:
<223> OTHER INFORMATION: Synthetic

<400> SEQUENCE: 14
tctgcctttg tccctagat                                                20

<210> SEQ ID NO 15
<211> LENGTH: 20
<212> TYPE: DNA
<213> ORGANISM: Artificial
<220> FEATURE:
<223> OTHER INFORMATION: Synthetic

<400> SEQUENCE: 15
aaccttcatt ccccaggact                                               20
```

ERBB3 BINDING PROTEIN COMPOSITIONS AND METHODS OF USE

CROSS-REFERENCE TO RELATED PATENT APPLICATIONS

This patent application claims the benefit of U.S. Provisional Patent Application No. 60/653,733, filed Feb. 17, 2005, the entire content of which is incorporated herein by reference.

STATEMENT OF FEDERALLY SPONSORED RESEARCH AND DEVELOPMENT

This work was supported in part by the National Institutes of Health, Grant Nos. NIH R01 CA76047 and R21 088882-01. Therefore, the U.S. Government has certain rights in the invention.

FIELD OF THE INVENTION

The present invention relates to compositions comprising or expressing a binding protein that represses cell-cycle genes regulated by transcription factors and methods of use.

BACKGROUND OF THE INVENTION

Prostate cancer is the second most prevalent cancer among men in the United States and ranks second to lung cancer in terms of annual mortality (Weir et al., 2003, *Annual Report to the Nation on the Status of Cancer, 1975-2000, featuring the uses of surveillance data for cancer prevention and control*, J. Natl. Cancer Inst., 95:1276-1299). Prostate cancer begins as an androgen-dependent tumor that undergoes clinical regression in response to pharmacological and surgical strategies that reduce testosterone concentration. Despite this treatment, the cancer eventually regrows as a lethal androgen or hormone-independent tumor (Feldman et al., 2001, *The Development of Androgen-Independent Prostate Cancer*, Nat. Rev. Cancer, 1:34-45).

The molecular basis for hormone-independent cancer progression is poorly understood. However, most androgen-independent prostate cancers still express androgen receptor (AR). Aberrant changes in AR signaling axis are postulated to play a fundamental role in the progression to androgen independence. The pathways involved in AR-mediated survival of prostate cancer cells in the absence of androgens include amplification or mutation of the AR, deregulation of growth factors or cytokines, and alteration of AR coregulators. Thus, the AR is a key molecule in pathways leading to androgen independence.

The AR is central to the initiation and growth of prostate cancer and to the therapeutic response of prostate cancer to hormones. AR continues to be expressed even in androgen-independent tumors and aberrant AR signaling is postulated to be an important mechanism of progression to androgen independence (Taplin et al., 2004, *Androgen Receptor: A Key Molecule in the Progression of Prostate Cancer to Hormone Independence*, J. Cell Biochem, 91:483-490). Both increased sensitivity of AR to androgens and activation of AR by growth factor and/or cytokines are proposed to account for androgen-independent growth (Feldman et al., 2001, *The Development of Androgen-Independent Prostate Cancer*, Nat. Rev. Cancer, 1:34-45). Clinically, upregulation of the AR has been recently demonstrated to be consistently associated with hormone refractory disease (Edwards et al., 2003, *Androgen Receptor Gene Amplification and Protein Expression in Hormone Refractory Prostate Cancer*, Br. J. Cancer, 89:552-556) (Taplin et al., 1995, *Mutation of the Androgen-Receptor Gene in Metastatic Androgen-Independent Prostate Cancer*, N. Engl. J. Med., 332:1393-1398). In a xenograft model, Chen et al. (Chen et al., 2004, *Molecular Determinants of Resistance to Antiandrogen Therapy*, Nat. Med. 10:33-39) recently reported that a two- to five-fold increase in AR MnRNA was the only change consistently associated with the development of androgen resistance. As a result, cells exhibit an increased sensitivity to low levels of androgen. In addition, androgen receptor antagonists are converted to agonists.

Thus, inhibition of AR expression is key to the design of new agents effective for treatment of prostate cancer (Isaacs et al., 2004, *Androgen Receptor Outwits Prostate Cancer Drugs*, Nat. Med., 10:26-27). Strategies that target the AR include the use of RNA interference, ribozymes, and antisense molecules to decrease AR mRNA (Eder et al., 2002, *Inhibition of LNCaP Prostate Tumor Growth In Vivo by an Antisense Oligonucleotide Directed Against the Human Androgen Receptor*, Cancer Gene Ther., 9:117-125) (Zegarra-Moro et al., 2002, *Disruption of Androgen Receptor Function Inhibits Proliferation of Androgen-Refractory Prostate Cancer Cells*, Cancer Res., 62:1008-1013), heat shock protein 90 inhibitors, such as 17 AAG, to destabilize AR protein (Solit et al., 2002, *17-Allylamino-17-Demethoxygeldanamycin Induces the Degradation of Androgen Receptor and HER-2/neu and Inhibits the Growth of Prostate Cancer Xenografts*, Clin. Cancer Res., 8:986-993), and pharmacological inhibitors of AR protein synthesis or function (Mitchell et al., 1999, *Resveratrol Inhibits the Expression and Function of the Androgen Receptor in LNCaP Prostate Cancer Cells*, Cancer Res., 59:5892-5895) (Zhu et al., 2001, *Silymarin Inhibits Function of the Androgen Receptor by Reducing Nuclear Localization of the Receptor in the Human Prostate Cancer Cell Line LNCaP*, Carcinogenesis, 22:1399-1403). However, the manipulation of endogenous AR corepressors to downregulate AR function has not yet been reported. Androgen receptor antagonists used in the treatment of prostate cancer cause recruitment of corepressor complexes to the AR, which underlies their inhibitory activity. Shang et al. (Shang et al., 2002, *Formation of the Androgen Receptor Transcription Complex*, Mol. Cell, 9:601-610) have demonstrated that the androgen antagonist bicalutamide recruits the repressors NCoR and SMRT to the AR bound to the PSA promoter. Chen et al. (Chen et al., 2004, *Molecular Determinants of Resistance to Antiandrogen Therapy*, Nat. Med., 10:33-39) demonstrated that increases in AR protein levels lead to a decrease in corepressor recruitment to AR-regulated promoters after bicalutamide treatment. Conceivably, the lack of association of AR with inhibitory coregulators might contribute to the increased AR transactivation potency in prostate cancer. The clinical resistance of these agents may reflect a failure of corepressor recruitment to the AR.

Another potential approach toward prostate cancer is gene therapy. Intraprostatic injection has been proposed as a minimally invasive technique to deliver gene therapy that could be readily performed by urologists or radiologists. The unsolved issue is to identify genes that would be efficacious for therapy. The most extensively studied gene therapeutic approach to date for prostate cancer is suicide gene therapy, typically involving the tumor-targeted delivery of genes encoding metabolic enzymes that convert systemically delivered, relatively innocuous prodrugs into highly toxic metabolites. However, the effectiveness of these strategies for human prostate cancer may be blunted because of their limited effect on slowly dividing prostate cells that require long term administration of prodrugs to increase the proportion of cells affected. Furthermore, these genes can be inhibited by anti-apoptotic proteins like Bcl-2 family members, which have been shown to be upregulated in progressive, hormone-refractory prostate cancer.

In view of the above, it is an object of the present invention to provide compositions and methods to manipulate endogenous genes. The compositions and methods can be used to repress cell-cycle genes and, thus, can be used to inhibit cancer, such as prostate cancer. This and other objects and advantages of the present invention, as well as additional inventive features, will become apparent from the detailed description provided herein.

BRIEF SUMMARY OF THE INVENTION

The present invention provides a method of repressing a cell-cycle gene, which is regulated by an E2F transcription factor, in a cell. The method comprises contacting the cell with a cell-cycle gene-repressing amount of ErbB3 binding protein (Ebp1).

The present invention further provides a method of inhibiting prostate cancer in a mammal. The method comprises administering to the mammal a prostate cancer-inhibiting amount of Ebp1.

A composition comprising an Ebp1-expressing viral vector is also provided. The viral vector expresses a cell-cycle gene-repressing amount of Ebp1. Also provided is a composition comprising polymer-packaged DNA comprising and expressing a cell-cycle gene-repressing amount of Ebp1.

BRIEF DESCRIPTION OF THE DRAWINGS

FIG. 1 sets forth the nucleotide sequence (SEQ ID NO: 1) of Ebp1 (GenBank Accession No. NM-006191).

FIG. 2 sets forth the amino acid sequence (SEQ ID NO: 2) of Ebp1 (GenBank Accession No. NM-006191).

DETAILED DESCRIPTION OF THE INVENTION

The present invention is predicated on the following observations. Ebp1 physically interacts with the N-terminal domain of AR, represses AR-mediated transactivation, and decreases BCL-2, AR, and ErbB2 protein levels in androgen-independent prostate cancer cells. The capability to inhibit transcriptional activity of the AR by targeting the N-terminal domain to block androgen-independent tumor growth presents a new direction for the development of Ebp1 mimetic peptide to the AR for the clinical management of hormone-refractory prostate cancer, given the fact that AR can be activated in the absence of cognate ligand by alternative pathways through a mechanism involving its N-terminal domain. Growth and transcription of AR-regulated reporter genes in response to androgen is decreased in ebp1 LNCaP transfectants but cells do not become androgen-independent. The agonist activity of the anti-androgen cyproterone acetate is abolished in ebp1 transfectants. This is of potential clinical interest also as mutation of AR leading to promiscuous activation has been postulated to be one mechanism of development of anti-androgen resistance. Endogenous Ebp1 is reduced in LAPC androgen-independent xenografts and in the C-81 androgen-independent cell line grown in vitro. Ebp1 inhibits tumorigenesis of LNCaP cells in a xenograft mouse model once Ebp1 is stably transfected. Ebp1 can downregulate androgen receptor and its target genes—the critical component in the design of prostate cancer treatment now that the AR, itself, has been documented to outwit prostate cancer drugs.

The present invention provides a method of repressing a cell-cycle gene, which is regulated by an E2F transcription factor, in a cell. The method comprises contacting the cell with a cell-cycle gene-repressing amount of Ebp1. The Ebp1 can be in the form of a nucleic acid, such as DNA or RNA, which directly or indirectly results in expression of the ErbB3 binding protein, or the protein itself. The cell can be in a tumor. The tumor can be in a mammal.

The cell can be contacted with Ebp1 by any suitable manner. For example, chemical transfection (e.g., calcium phosphate, lipid complexes, or protein complexes) or physical transfection (e.g., electroporation, microinjection, or ballistics) can be used to introduce Ebp1-expressing nucleic acids, in accordance with methods known in the art. Electroporation with high-voltage electric impulses can transiently increase cell membrane permeability, allowing large molecules, including cytotoxic agents, to enter the cell. Cells can be contracted with Ebp1 protein by direct contact, such as by injection into or in the vicinity of the cell in which repression of a cell-cycle gene is desired.

The Ebp1 can be expressed from a vector, such as a viral vector, in which case the cell is contacted with the viral vector. Examples of suitable viral vectors include lentiviral vectors, retroviral vectors, adenoviral vectors, adeno-associated viral vectors, and herpes viral vectors. The viral vector can be targeted to a cell-surface molecule if desired. Alternatively or additionally, the cell, in which repression of a cell-cycle gene is desired, can be contacted directly. For example, if the cell is in a tumor, the viral vector can be injected into or in the immediate vicinity of the tumor.

The nucleotide sequence of Ebp1 is set forth in FIG. 1 as SEQ ID NO: 1. The amino acid sequence of Ebp1 is set forth in FIG. 2 as SEQ ID NO: 2. It is understood by one of ordinary skill in the art that, due to the degeneracy of the genetic code, more than one nucleotide sequence can encode for the same amino acid sequence. All nucleotide sequences the encode Ebp1 can be used in the context of the present invention. One of ordinary skill in the art will also appreciate that such nucleotide and amino acid sequences can involve the use of nonnaturally occurring or modified nucleotides or amino acids, respectively. Also appreciated is that nucleotide and amino acid sequences can be modified somewhat, such as by insertion, deletion, and other types of mutations, without adversely affecting the activity of the protein. In some instances, such modifications can enhance the activity of the protein.

The use of nonnaturally occurring or modified nucleotides and amino acids, the introduction of mutations in nucleotide and amino acid sequences, and the construction of viral vectors is within the skill in the art, as is the targeting of viral vectors to cell-surface molecules. See, e.g., Sambrook et al., *Molecular Cloning: A Laboratory Manual*, Cold Spring Harbor Laboratory, 3$^{rd}$ edition, 2001; Federico, *Lentivirus Gene Engineering Protocols*, Humana Press, 2003; and Machida, *Viral Vectors for Gene Therapy: Methods and Protocols*, Humana Press, 2002.

Alternatively, the Ebp1 can be expressed from polymer-packaged DNA, in which case the cell is contacted with the polymer-packaged DNA. See, e.g., Mixson, U.S. Pat. No. 6,080,728, which is hereby specifically incorporated by reference.

In view of the above, the present invention provides a method of inhibiting prostate cancer in a mammal. The method comprises administering to the mammal a prostate cancer-inhibiting amount of Ebp1, whereupon the prostate cancer in the mammal is inhibited.

What constitutes a "cell-cycle gene-repressing amount" or a "prostate cancer-inhibiting amount" of Ebp1 can be determined in accordance with dosage range finding techniques as are known in the art. Typically, if a viral vector is used, a cell should be contacted with about 10 viral particles per cell. If liposomes or protein-complexed or polymer-packaged DNA is used, a cell should be contacted with about 1.5 µl per 50,000 cells. Cell-targeting methods can reduce the amount of particles needed, as can chemical/physical transfection of uncomplexed nucleic acids or proteins.

The present invention further provides compositions. In one embodiment, the present invention provides a composition comprising an Ebp1-expressing viral vector. The viral vector expresses a cell-cycle gene-repressing amount of Ebp1. The viral vector can be a lentiviral vector. Alternatively or additionally, the viral vector can be targeted to a cell-surface molecule.

In another embodiment, the present invention provides a composition comprising polymer-packaged DNA comprising and expressing a cell-cycle gene-repressing amount of Ebp1. Pharmaceutical compositions are known in the art. See e.g., Gennaro, *Remington: The Science and Practice of Pharmacy*, Lippincott, Williams & Wilkins, 20$^{th}$ ed., 2003.

The following example serves to illustrate the present invention. The example is not, however, intended to limit the scope of the present invention in any way.

EXAMPLE

Cell culture: All cell lines were obtained from the American Type Culture Collection (Manassas, Va.) and maintained at 37° C. in a humidified atmosphere of 5% $CO_2$ in air. Cell lines were routinely cultured in RPMI 1640 media supplemented with 10% fetal bovine serum (FBS).

Microarray Analysis: First and second strand cDNA were synthesized from 5-15 µg of total RNA at Genome Explorations (Nashville, Tenn.) using the SuperScript Double-Stranded cDNA Synthesis Kit (Gibco Life Technologies, Gaithersburg, Md.) and an oligo-$dT_{24}$-T7 (5'-GGC CAG TGA ATT GTA ATA CGA CTC ACT ATA GGG AGG CGG-3') (SEQ ID NO: 3) primer according to the manufacturer's instructions. cRNA was synthesized labeled with biotinylated UTP and CTP by in vitro transcription using the T7 promoter-coupled, double-stranded cDNA as template and the T7 RNA Transcript Labeling Kit (ENZO Diagnostics Inc., Farmingdale, N.Y.). The fragmented cRNA was hybridized for U133A oligonucleotide arrays (Affymetrix, Santa Clara, Calif.) containing ~33,000 full-length annotated genes, together with additional probe sets designed to represent EST sequences. The arrays were then stained with phycoerythrein-conjugated streptavidin (Molecular Probes, Eugene, Oreg.), and the fluorescence intensities were determined using a laser confocal scanner (Hewlett-Packard, Palo Alto, Calif.). The scanned images were analyzed using Microarray software (Affymetrix). Sample loading and variations in staining were standardized by scaling the average of the fluorescent intensities of all genes on an array to constant target intensity for all arrays used. The signal intensity for each gene was calculated as the average intensity difference, represented by [E(PM–MM)/(number of probe pairs)], where PM and MM denote perfect-match and mismatch probes. Data analysis was conducted using Microarray Suite 5.0 (Affymetrix) following user guidelines. Only genes with a minimum expression level of 500 were included in this analysis. Only genes whose expression varied more than three-fold with a p value of <0.05 were considered to be significantly different between the two cell lines. AR-regulated genes include the Androgen Receptor (AR), PSA (kallikrein 3), Kallikrein 2, POV-1, TMPRSS2, and prostate-derived factor.

Real-Time Quantitative Reverse-Transcription PCR: The method of Nakanish et al. (Nakanishi et al., 2003, *Quantitative Analysis of Breast Cancer Resistance Protein and Cellular Resistance to Flavopiridol in Acute Leukemia Patients*, Clin. Cancer Res., 9: 3320-3328) was used as previously described. RNA was extracted (Zhang et al., 2003, *Repression of E2F1-Mediated Transcription by the ErbB3 Binding Protein Ebp1 Involves Histone Deacetylases*, Nucleic Acids Research, 31: 2168-2177) and cDNA was synthesized using random hexanucleotides from 1 µg of RNA. Real-time quantitative RT-PCR was then performed on the LightCycler (Roche, Indianapolis, Ind.) platform to determine the relative mRNA levels of Ebp1, AR, kallikrein-2 and POV-1. The following forward and reverse primers were selected using Primer Express software and synthesized by Core Laboratory of University of Maryland School of Medicine: Ebp1, sense: 5'-GCACGCCAATAGAAGG -3' (SEQ ID NO: 4) and antisense: 5'-GTAAACGGCATGGCATC-3'b (SEQ ID NO: 5), sense: 5'-AAGGCTATGAATGTCAGCCCA-3' (SEQ ID NO: 6) and antisense: 5° CATTGAGGCTAGAGAG-CAAGGC-3' (SEQ ID NO: 7), Kallikrein-2, sense: 5'-CATC-CAGTCTCGGATTG-3' (SEQ ID NO: 8) and antisense: 5'-CTCATATTGTAGAGCGGGT-3' (SEQ ID NO: 9), POV-1, sense: 5'-AGTGCTGTGTTCGCCTTG-3' (SEQ ID NO: 10) and antisense: 5'-CACCTCAGAGCCGCTAAG-3' (SEQ ID NO: 11), Actin, sense: 5' GCT ATC CAG GCT GTG CTA TC-3' (SEQ ID NO: 12) and antisense TGT CAC GCA CGA TTT CC-3' (SEQ ID NO: 13). An SRBR Green PCR Kit was used (Applied Biosystems, Foster City, Calif.), and the analyses were performed in duplicate or triplicate in a total volume of 15 µl including 0.9 µl of 25 mM $MgCl_2$, 1.5 µl SYBR Green I, 0.3 µl Enzyme Mix, 0.75 µl of each primer (50 ng/µl), and 2 µl of cDNA synthesized with random hexamers. Target mRNA values were normalized using actin mRNA as an internal control. The relative quantitation of gene expression was performed using the comparative $\Delta\Delta\ C_t$ (threshold method) using β-actin as an internal control (Nikitakis et al., 2002, *The Nonsteroidal Anti-Inflammatory Drug Sulindac Causes Down-Regulation of Signal Transducer and Activator of Transcription 3 in Human Oral Squamous Cell Carcinoma Cells*, Cancer Research, 62:1004-1007).

Western Blot Analysis: Briefly, total cell extracts were prepared by direct lysis of cells with buffer containing 50 mM Tris-HCl (pH 7.4), 1 mM EDTA, 250 mM NaCl, 1% Triton X-100, 0.5 mM dithiothreitol (DTT) and 1 mM phenylmethylsulfonyl (PMSF). Protein concentrations were measured using a detergent compatible kit (BioRad, Hercules, Calif.). Proteins were resolved by SDS-PAGE and analyzed by Western blotting as described (Xia et al., 2001, *Analysis of the Expression Pattern of Ebp1, an ErbB-3-Binding Protein*, Biochem. Biophys. Res. Commun., 289:240-244). The AR antibody was from Santa Cruz Biotechnology (Santa Cruz, Calif.), the Ebp1 antibody from Upstate (Lake Placid, N.Y.), the polyclonal antibody to actin from Sigma (St. Louis, Mo.), and the POV-1 antibody was a gift of Dr. Rodrigo Chugai, National Cancer Institute.

ChIP Assays: The method of Shang et al. (Shang et al., 2002, *Formation of the Androgen Receptor Transcription Complex*, Mol. Cell, 9:601-610) was used. Briefly, LNCaP ebp1 transfectants were grown in RPMI 1640 medium supplemented with 5% charcoal-stripped FBS (Sigma). After 3 days of culture, cells were treated with 5 µM bicalutamide for one hour, washed with phosphate-buffered saline (PBS) and centrifuged for 5 min. The pellets were then resuspended in 0.3 ml of lysis buffer (1% SDS, 10 mM EDTA, 50 mM Tris-HCl, pH 8.1, and 1×protease inhibitor cocktail (Roche)). DNA was sheared on ice to the appropriate lengths (~500 basepairs) with 3 sets of 10-second pulses at 20% maximal output, followed by centrifugation for 10 min at 13,000 rpm at 4° C. Supernatants were mixed, aliquoted and diluted in NET-N buffer (20 mM Tris-HCl, pH 8.0, 150 mM NaCl, 10 mM EDTA, 0.5% NP-40, 1.5 mM $MgCl_2$, 10% glycerol and protease inhibitor cocktail) for a final volume of 1.5 ml. A portion of the diluted cell supernatant (1%) was kept to have crosslinks reversed and quantitate the amount of DNA present in samples for the PCR protocol. After pre-clearing with salmon sperm DNA/protein A agarose slurry for 30 min at 4° C., immunoprecipitation was performed overnight on a rotary shaker at 4° C. with specific antibodies or pre-immune IgG as a control. The samples were then mixed with sonicated salmon sperm DNA (100 µg/ml) and Protein A/G agarose (Oncogene Research Products, San Diego, Calif.) for another 6 h incubation. Agarose beads were washed sequentially in low salt, high salt, LiCl and TE buffer provided with a kit from Upstate and extracted two times with freshly prepared elution buffer (1% SDS, 0.1 M $NaHCO_3$). Eluates were pooled and incubated at 65° C. for 6 h to reverse the formaldehyde crosslinks. DNA was purified by phenol/chloroform extraction, and precipitated in the presence of 0.3 M sodium acetate and 20 µg tRNA in 2 volumes of ethanol at −20° C. overnight. The DNA pellets were dissolved in 50 µl of water. Nested PCR amplification of a 210 bp PSA promoter fragment (−250 to −39) was carried out using a 5' primer 5'-TCTGCCTTTGTC-CCCTAGAT-3' (SEQ ID NO: 14) and a 3' primer 5'-AACCT-TCATTCCCCAGGACT -3' (SEQ ID NO: 15). The PCR products were resolved on 2.5% agarose gels and visualized with ethidium bromide.

Cell Growth Assays: To measure growth in complete media, cells ($2 \times 10^4$) were seeded in triplicate in individual wells of 12-well tissue culture plates in RPMI-1640 with 10% FBS and cultured for the indicated number of days. Cells were trypsinized, stained with Trypan Blue (0.4%), and counted in a hemacytometer. For soft agar growth assays, increasing concentrations of cells (as indicated) were plated in 35 mm petri dishes in complete media and 0.3% Difco Bacto Agar over an 0.5% agar layer. Colonies were counted after 10 days of incubation. For studies assessing the effect of dihydrotestosterone (DHT) on cell growth, cells ($2 \times 10^4$) were plated in 12-well plates in complete media. After a 24-hour attachment period, the medium was replaced with steroid-free medium [phenol red-free RPMI 1640 and 5% charcoal-stripped FBS (Sigma)] for 48 hours. The final concentration of testosterone in the steroid-reduced media was less than 5 pM. After 48 hours of steroid depletion, cells were re-fed with fresh steroid-reduced medium with or without the indicated concentrations of DHT and/or bicalutamide (10 µM), and total cell numbers were assessed 7 days later.

Luciferase Reporter Assays: Vector control or ebp1-transfected LNCaP ($5 \times 10^4$) cells were plated in twelve-well plates in complete media. When cells reached 50-60% confluence, they were transfected with 0.5 µg of MMTV-luc using the Fugene-6 reagent (Roche). Cells were also transfected with the RL-TK vector as an internal control. Complete medium was replaced after 24 h with phenol red and serum-free DMEM-F12 or RPMI 1640 with or without 10 nM R1881 (Slagsvold et al., 2001, *DNA Binding-Independent Transcriptional Activation by the Androgen Receptor Through Triggering of Coactivators*, J. Biol. Chem., 276: 31030-6) (NEN, Boston, Mass.) or cyproterone acetate (Sigma). Luciferase activity was determined as previously described using a Dual-Luciferase kit (Promega, Madison, Wis.). The activities of renilla luciferase were used to normalize any variations in transfection efficiency. The promoter activities of each plasmid construct were calculated as the firefly-renilla luciferase activity ratios. All transfection experiments were carried out in triplicate wells and repeated three times.

In Vivo Studies in SCID Mice: Male SCID mice, 4-6 weeks of age, were purchased from the National Cancer Institute (Frederick, Md.). Animals were housed in a pathogen-free environment under controlled conditions of light and humidity and received food and water ad libitum. LNCaP cells were grown in complete medium and 800 µg/ml of G418 until 80% confluent. Cells were scraped into phosphate-buffered saline (PBS), collected by centrifugation, and suspended in Matrigel (10 mg/ml) (Collaborative Research, Waltham, Mass.) at $1 \times 10^7$ cells/ml. Each mouse received s.c. injections at one site on each flank with 100 µl of cell suspension. Tumors were measured three times a week with calipers, and tumor volumes were calculated by the formula $0.5236 \times r_1^2 \times r_2$ (r1<r2). The animal protocols were approved by the Institutional Animal Care and Use Committee at the University of Maryland.

After sacrifice, tumors were excised and fixed in 10% buffered neutral formalin. Sections of formalin-fixed, paraffin-embedded tissues were cut to 5 µm. Slides were stained with an Ebp1 antibody (Upstate) diluted 1:50 using the standard avidin-biotin method (Vector Labs, Burlinghame, Calif.). Peroxidase activity was localized by the diaminobenzidine tetrachloride peroxidase reaction with Harris hematoxylin as a counterstain.

Measurement of PSA levels: Serum PSA levels were determined using a PSA ELISA kit from DSL, Inc (Webster, Tex.). Briefly, 25 µl of serum diluted in 1:5 in DPBS or conditioned media was mixed with assay buffer to a final volume of 75 µl and added to duplicate wells in the 96 well plates that had been coated with an anti-PSA antibody. Following a 1 h incubation and extensive washing of the plate, the wells were treated for 30 min with a second anti-PSA antibody labeled with horseradish peroxidase. After washing, the wells were treated with a tetramethylbendizine substrate for 10 min, and absorbance was read at 450 nm.

Statistical Analysis: Results of growth and luciferase assays were analyzed using a two-tailed Students t-test. Significance was established at $P<0.05$. The proportion of growing tumors in control versus ebp1 transfectants and the rate of growth were tested using Fisher's exact test, two-sided. AP<0.05 was considered to be statistically significant.

Ectopic expression of Ebp1 downregulates androgen-regulated genes: Gene expression profiling of LNCaP cells stably transfected with ebp1 was used to determine the range of androgen-dependent genes affected by Ebp1 overexpression. These cells overexpress Ebp1 protein between two- and three-fold (Zhang et al., 2002, *Repression of Androgen Receptor Mediated Transcription by the ErbB-3 Binding Protein Ebp1*, Oncogene, 21: 5609-5618). Changes in gene expression were measured using microarray analysis of 33,000 transcripts on the Affymetrix U133A chip. To compile a list of differentially regulated genes, only those genes that were activated or repressed at least 3-fold (p <0.05, 500 minimum expression units) were included. Of 8,000 genes that were evaluable, the expression of 167 genes was found to differ significantly between the two cell lines. Forty-one genes were induced and 126 were repressed. Seventy-two of these genes have HUGO approved names. Six androgen-responsive genes were found to be downregulated at least three-fold in ebp1-overexpressing cells as compared to controls. These include the Androgen Receptor (3.7 fold decrease), PSA (3.7 fold decrease) as previously reported (Zhang et al., 2002, *Repression of Androgen Receptor Medi-* ated Transcription by the ErbB-3 Binding Protein Ebp1, Oncogene, 21: 5609-5618), Kallikrein 2 (3.2 fold decrease), POV-1 (5.0 fold decrease), TMPRSS2 (3.2 fold decrease), and prostate-derived factor (3.2 fold decrease). The Kallikrein 2 gene is regulated by AR, predominantly expressed in prostate tissue, secreted by LNCaP cells, and 78% homologous to PSA. The potential value of Kallikrein 2 in prostate cancer detection is strongly suggested by recent studies (Partin et al., *Use of Human Glandular Kallikrein 2 for the Detection of Prostate Cancer: Preliminary Analysis*, Urology, 54:839-845). The POV-1 gene encodes a transcript for a novel L amino acid transporter (Babu et al., 2003, *Identification of a Novel System L Amino Acid Transporter Structurally Distinct from Heterodimeric Amino Acid Transporters*, J. Biol. Chem., 278:43838-43845) that was found to be upregulated in aggressive prostate carcinoma (Chuaqui et al., 1997, *Identification of a Novel Transcript Up-Regulated in a Clinically Aggressive Prostate Carcinoma*, Urology, 50:302-307). The TMPRSS2 gene is androgen-regulated and also highly expressed in prostate and prostate cancer (Afar et al., 2001, *Catalytic Cleavage of the Androgen-Regulated TMPRSS2 Protease Results in its Secretion by Prostate and Prostate Cancer Epithelia*, Cancer Res., 61:1686-1692). Prostate-derived factor, a member of the bone morphogenetic protein family, also has been shown to be androgen-regulated and is expressed in high levels in the prostate (Paralkar et al., 1998, *Cloning and Characterization of a Novel Member of the Transforming Growth Factor-Beta/Bone Morphogenetic Protein Family*, J. Biol. Chem., 273:13760-13767).

The results of the microarray analysis were validated using real-time quantitative reverse-transcription PCR, Western blot, and ELISA methods. Real-time PCR methods indicated that AR mRNA was down-regulated more than 2-fold in ebp1 transfectants. Western blot analysis indicated that AR protein was decreased more than five-fold in LNCaP ebp1 transfectants. The expression of POV-1 mRNA and protein were each decreased about two-fold. PSA secretion in the conditioned media of ebp1 and vector control cells was assessed by ELISA. Levels of secreted PSA in the control cells were similar to those previously reported (Lee et al., 1995, *Regulation of Proliferation and Production of Prostate-Specific Antigen in Androgen-Sensitive Prostatic Cancer Cells, LNCaP, by Dihydrotestosterone*, Endocrinology, 136:796-803). Results showed that secreted PSA protein was downregulated 10-fold in ebp1 transfectants as compared to controls. Finally, kallikirein-2 mRNA expression was decreased approximately 40%.

Chromatin immunoprecipitation experiments were conducted. Ebp1 transfectants were serum-starved and then treated with bicalutamide for one hour. HDAC2 was recruited to the PSA promoter after exposure to bicalutamide as previously reported (Shang et al., 2002, *Formation of the Androgen Receptor Transcription Complex*, Mol. Cell, 9:601-610). Ebp1 was not associated with the promoter in the absence of bicalutamide, but was recruited to the PSA promoter after bicalutamide exposure.

The data indicating that Ebp1 is recruited to the PSA promoter in the presence of biclautamide suggest that Ebp1 may be involed in the response to anti-androgens and play a role in the development of the androgen-independent phenotype. The presence of Ebp1 was assayed in models of androgen independence. The C-81 LNCaP subline has been made androgen-independent by continuous high level passage in complete media (Igawa et al., 2002, *Establishment and Characterization of Androgen-Independent Human Prostate Cancer LNCaP Cell Model*, Prostate, 50:222-235). The LAPC-4 model has been extensively characterized as to its ability to recapitulate the progression of prostate cancer. This xenograft has wild-type AR receptor and grows as androgen-dependent cancers in male SCID mice. These tumors regress in response to androgen ablation but eventually regrow as androgen-independent tumors that overexpress ErbB2 (Klein et al., 1997, *Progression of Metastatic Human Prostate Cancer to Androgen Independence in Immunodeficient SCID Mice*, Nat. Med., 3:402-408). LAPC xenografts that were grown in either intact or castrated mice were also examined. The results indicated that expression of Ebp1 protein was decreased in both C-81 and LAPC androgen-independent sublines.

Growth Characteristics of LNCaP ebp1 transfectants: The growth rate of the ebp1-transfected cells in complete media was compared to that of cells transfected with the empty vector. The growth rate of the ebp1 transfectants was significantly decreased (p<0.05) as compared with that of the vector control. The doubling time for ebp1 transfectants increased to 72 hours from 48 hours for the vector control line.

The soft agar growth of ebp1 transfectants was also examined. LNCaP vector controls and ebp1 transfectants were seeded at concentrations between $1 \times 10^4$ and $1 \times 10^5$ cells per dish and colony growth in soft agar assessed ten days later. Ectopic expression of ebp1 decreased colony growth approximately 90% at the highest cell concentration tested.

The sensitivity of ebp1 transfectants to DHT was also examined. Both LNCaP vector controls and ebp1 transfectants were placed in serum-free media and then stimulated with DHT. The growth of the vector controls was inhibited approximately 70% by the withdrawal of androgens as previously reported (Igawa et al., 2002, supra). The growth of ebp1 transfectants was inhibited 60%. Thus, ebp1 transfectants had not become androgen-independent. As previously reported (Igawa et al., 2002, supra), DHT at increasing concentrations stimulated the growth of LNCaP vector controls with a maximal 250% stimulation at $10^{-9}$ M DHT as compared to no DHT. In contrast, DHT at $10^{-9}$ M only slightly (35%) stimulated the growth of Ebp1 transfectants.

The effect of the anti-androgen bicalutamide on DHT-stimulated growth was also examined. The DHT-stimulated growth of both LNCaP vector controls and ebp1-transfected cells was completely suppressed by 10 µM bicalutamide.

The effect of the stable overexpression of Ebp1 on the transactivation of the MMTV-luciferase (MMTV-luc) reporter gene induced by R1881 and the partial agonist cyproterone acetate was also analyzed. Addition of R1881 ($10^{-8}$ M) led to a 20-fold activation of luciferase activity of LNCaP vector controls. Cyproterone acetate ($10^{-7}$ M) induced a 5-fold activation of the AR as previously reported (Dotzlaw et al., 2002, *The Amino Terminus of the Human AR is Target for Corepressor Action and Antihormone Agonism*, Mol. Endocrinol, 16:661-673) and enhanced the transcriptional response in the presence of R1881. In contrast, neither R1881 nor cyproterone acetate nor the combination thereof stimulated AR activation in ebp1 transfectants.

The effect of a range of concentrations of cyproterone acetate on AR transactivation was also examined. LNCaP vector controls and ebp1 transfectants were transfected with the MMTV-luc reporter and their response to increasing concentrations of cyproterone acetate was tested. Cyproterone acetate induced activation of AR at concentrations of $10^{-6}$ to $10^{-8}$ as previously reported (Veldscholte et al., 1990, *A Mutation in the Ligand Binding Domain of the Androgen Receptor of Human LNCaP Cells Affects Steroid Binding Characteristics and Response to Anti-Androgens*, Biochem. Biophys. Res. Commun., 173:534-540). In contrast, cyproterone acetate failed to induce activation of the AR in the ebp1 transfectants at any concentration tested.

Ebp1 expression suppresses growth of prostate cancer xenografts: The effect of ectopic expression of ebp1 on the tumorigenicity of LNCaP cells was examined. Ebp1- and vector-transfected cells were injected subcutaneously into SCID mice, and tumor growth was monitored. Tumor growth was first noted in both groups at day 20. However, on day 20, tumors were observed at only 10% of the ebp1 inoculation sites, as opposed to 35% of the sites for vector controls. At the end of the study, tumors had developed at more than 85% of the sites injected with the vector control cells, while less than 40% of sites inoculated with ebp1 transfectants developed tumors. This difference was significant at p=0.04 by Fisher's exact test, two-sided. The average tumor volumes were also significantly different between the ebp1 transfectants and vector controls. Average tumor volumes observed at the end of the study were 268±70 mm$^3$ as compared with 1214±168 mm$^3$ for the vector controls (p=0.0003). In addition, the growth rate was also slower for ebp1 transfectants at all time points measured (p=0.0001). Immunohistochemical staining of tissue sections of the tumors indicated that Ebp1 expression was equivalent in both groups. Real-time PCR of Ebp1 mRNA extracted from the tumors showed no change between the two groups. Thus, cells that grew to form tumors had lost overexpression of the transgene.

Thus, Ebp1, an ErbB3 binding protein, is a potent repressor of AR signaling. Gene expression profiling identified that a cohort of AR target genes, potentially involved in androgen-independent growth of prostate cancer cells, was down-regulated in cells with only moderate Ebp1 expression as compared with the vector-transfected cells. These results were validated by Real-Time Quantitative RT-PCR, Western blot and ELISA assays. Therefore, an AR corepressor can down-regulate levels of AR protein.

A reduction in AR activity or expression appears to be a key component of prostate cancer treatment. Overexpression of an AR corepressor, Ebp1, reduces AR protein levels and transcripton of AR-regulated genes in LNCAP cells, resulting in a less tumorigenic phenotype. In addition, endogenous Ebp1 expression was lost in two different models of androgen-independent prostate cancer growth.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of repressing a cell-cycle gene, which is regulated by a level of an E2F transcription factor, in a cell in a tumor in a mammal, which method comprises contacting the cell in the tumor in the mammal with a nucleic acid encoding Ebp1 protein which expresses in the cell in the tumor in the mammal a cell-cycle gene repressing amount of Ebp1 protein, whereupon the cell-cycle gene is repressed.

2. The method of claim 1, wherein the Ebp1 protein is expressed from a viral vector, in which case the cell is contacted with the viral vector.

3. The method of claim 2, wherein the viral vector is a lentiviral vector.

4. The method of claim 2, wherein the viral vector is targeted to a cell-surface molecule.

5. The method of claim 2, wherein the viral vector is injected into or in the immediate vicinity of the tumor.

6. The method of claim 1, wherein the Ebp1 protein is expressed from polymer-packaged DNA, in which case the cell is contacted with the polymer-packaged DNA.

7. The method of claim 1, wherein the Ebp1 protein is overexpressed.

8. The method of claim 1, wherein the nucleic acid encoding Ebp1 protein is set forth in SEQ ID NO: 1.

9. A method of suppressing or slowing the growth of prostate cancer in a mammal, which method comprises administering to the mammal a nucleic acid encoding Ebp1 protein, wherein Ebp1 protein is expressed in the prostate cancer in the mammal, whereupon growth of the prostate cancer in the mammal is suppressed or slowed.

10. The method of claim 9, wherein the Ebp1 protein is expressed from a viral vector, in which case the prostate cancer is contacted with the viral vector.

11. The method of claim 10, wherein the viral vector is a lentiviral vector.

12. The method of claim 10, wherein the viral vector is targeted to a cell-surface molecule.

13. The method of claim 10, wherein the viral vector is injected into or in the immediate vicinity of a tumor in the prostate.

14. The method of claim 9, wherein the Ebp1 protein is expressed from polymer-packaged DNA, in which case the cell is contacted with the polymer-packaged DNA.

15. The method of claim 9, wherein the Ebp1 protein is overexpressed.

16. The method of claim 9, wherein the nucleic acid encoding Ebp1 protein is set forth in SEQ ID NO: 1.

17. A method of treating prostate cancer in a mammal, which method comprises administering to the mammal a nucleic acid encoding Ebp1 protein, wherein Ebp1 protein is expressed in the prostate cancer in the mammal, whereupon the prostate cancer in the mammal is treated.

18. The method of claim 17, wherein the Ebp1 protein is expressed from a viral vector, in which case the prostate cancer is contacted with the viral vector.

19. The method of claim 18, wherein the viral vector is a lentiviral vector.

20. The method of claim 18, wherein the viral vector is targeted to a cell-surface molecule.

21. The method of claim 18, wherein the viral vector is injected into or in the immediate vicinity of a tumor in the prostate.

22. The method of claim 17, wherein the Ebp1 protein is expressed from polymer-packaged DNA, in which case the prostate cancer is contacted with the polymer-packaged DNA.

23. The method of claim 17, wherein the Ebp1 protein is overexpressed.

24. The method of claim 17, wherein the nucleic acid encoding Ebp1 protein is set forth in SEQ ID NO: 1.

* * * * *